United States Patent [19]

Takai et al.

[11] Patent Number: 5,378,810
[45] Date of Patent: Jan. 3, 1995

[54] MUTANT SMG P21 PROTEIN WITH GTP BINDING ACTIVITY

[75] Inventors: Yoshimi Takai, Kobe; Jun Kondo; Yasushi Matsui, both of Machida; Yutaka Teranishi, Sagamihara; Rie Matsui, Machida, all of Japan

[73] Assignee: Mitsubishi Kasei Corporation, Tokyo, Japan

[21] Appl. No.: 949,105

[22] Filed: Sep. 21, 1992

Related U.S. Application Data

[60] Division of Ser. No. 814,205, Dec. 20, 1991, which is a continuation of Ser. No. 358,835, May 30, 1989, abandoned.

[30] Foreign Application Priority Data

May 31, 1988 [JP] Japan ............................... 63-133584
Nov. 11, 1988 [JP] Japan ............................... 63-284860
May 9, 1989 [JP] Japan ............................... 1-115831

[51] Int. Cl.$^6$ .......................... C07K 13/00; C12N 15/00
[52] U.S. Cl. ............................. 530/350; 435/69.1; 435/69.4; 435/172.1; 530/399
[58] Field of Search ............... 530/350, 399; 435/69.1, 435/69.4, 172.1

[56] References Cited

U.S. PATENT DOCUMENTS

4,870,161  9/1989  Spiegel .
4,877,867 10/1989  Shalitin ............................ 530/387
5,104,975  4/1992  McCormick et al. ............. 530/350

OTHER PUBLICATIONS

Chemical Abstracts, vol. 107, No. 9, 1987 p. 159, Abstract No. 71715a, H. Itoh, et al.

The Journal of Biological Chemistry, vol. 263, No. 6, 1988, pp. 2897-2904, A. Kikuchi, et al.
The Journal of Biological Chemistry, vol. 263, No. 35, 1988, pp. 18965-18971, M. Kawata, et al.
The Journal of Biological Chemistry, vol. 264, No. 3, 1989, pp. 1877-1881, T. Ohmori, et al.
The Journal of Biological Chemistry, vol. 263, No. 23, 1988, pp. 11071-11074, Y. Matsui, et al.
Biochemical and Biophysical Research Communications,, vol. 156, No. 2, 1988, pp. 889-897, K. Ikeda, et al.
Biochemical and Biophysical Research Communications, vol. 157, No. 3, 1988, pp. 851-860, M. Hoshijima, et al.
Jackson B. Gibbs, et al. TIBS Sep. 1985, pp. 350-353.

*Primary Examiner*—Garnette D. Draper
*Assistant Examiner*—Sally P. Teng
*Attorney, Agent, or Firm*—David G. Conlin; Ronald I. Eisenstein

[57] ABSTRACT

The present invention provides a GTP binding protein containing the following amino acid sequence, with a molecular weight of about 22K dalton and having GTP binding activity which is inhibited by N-ethyl-maleimide and GTP hydrolyzing activity:

Thr-Ile-Glu-Asp-Ser-Tyr, and a method for the production of a GTP binding protein, which comprises introducing a DNA fragment containing DNA that encodes the GTP binding protein into a cloning site present at the downstream to a promoter of an expression vector, then introducing the expression vector thus constructed into a host, culturing said host, thereby expressing and accumulating the GTP binding protein and then collecting thereof.

1 Claim, 7 Drawing Sheets

Fig.1(i)

```
  1                    5                         10
Met-Arg-Glu-Tyr-Lys-Leu-Val-Val-Leu-Gly- 11                   15                         20
Ser-Gly-Gly-Val-Gly-Lys-Ser-Ala-Leu-Thr- 21                   25                         30
Val-Gln-Phe-Val-Gln-Gly-Ile-Phe-Val-Glu- 31                   35                         40
Lys-Tyr-Asp-Pro-Thr-Ile-Glu-Asp-Ser-Tyr- 41                   45                         50
Arg-Lys-Gln-Val-Glu-Val-Asp-Cys-Gln-Gln- 51                   55                         60
Cys-Met-Leu-Glu-Ile-Leu-Asp-Thr-Ala-Gly- 61                   65                         70
Thr-Glu-Gln-Phe-Thr-Ala-Met-Arg-Asp-Leu- 71                   75                         80
Tyr-Met-Lys-Asn-Gly-Gln-Gly-Phe-Ala-Leu- 81                   85                         90
Val-Tyr-Ser-Ile-Thr-Ala-Gln-Ser-Thr-Phe- 91                   95                        100
Asn-Asp-Leu-Gln-Asp-Leu-Arg-Glu-Gln-Ile- 101                  105                        110
Leu-Arg-Val-Lys-Asp-Thr-Glu-Asp-Val-Pro- 111                  115                        120
Met-Ile-Leu-Val-Gly-Asn-Lys-Cys-Asp-Leu-
```

Fig.1(i)

```
  1                       5                          10
Met-Arg-Glu-Tyr-Lys-Leu-Val-Val-Leu-Gly- 11                      15                          20
Ser-Gly-Gly-Val-Gly-Lys-Ser-Ala-Leu-Thr- 21                      25                          30
Val-Gln-Phe-Val-Gln-Gly-Ile-Phe-Val-Glu- 31                      35                          40
Lys-Tyr-Asp-Pro-Thr-Ile-Glu-Asp-Ser-Tyr- 41                      45                          50
Arg-Lys-Gln-Val-Glu-Val-Asp-Cys-Gln-Gln- 51                      55                          60
Cys-Met-Leu-Glu-Ile-Leu-Asp-Thr-Ala-Gly- 61                      65                          70
Thr-Glu-Gln-Phe-Thr-Ala-Met-Arg-Asp-Leu- 71                      75                          80
Tyr-Met-Lys-Asn-Gly-Gln-Gly-Phe-Ala-Leu- 81                      85                          90
Val-Tyr-Ser-Ile-Thr-Ala-Gln-Ser-Thr-Phe- 91                      95                         100
Asn-Asp-Leu-Gln-Asp-Leu-Arg-Glu-Gln-Ile- 101                     105                         110
Leu-Arg-Val-Lys-Asp-Thr-Glu-Asp-Val-Pro- 111                     115                         120
Met-Ile-Leu-Val-Gly-Asn-Lys-Cys-Asp-Leu-
```

Fig.1(ii)

```
121                 125                      130
Glu-Asp-Glu-Arg-Val-Val-Gly-Lys-Glu-Gln- 131                 135                      140
Gly-Gln-Asn-Leu-Ala-Arg-Gln-Trp-Cys-Asn- 141                 145                      150
Cys-Ala-Phe-Leu-Glu-Ser-Ser-Ala-Lys-Ser- 151                 155                      160
Lys-Ile-Asn-Val-Asn-Glu-Ile-Phe-Tyr-Asp- 161                 165                      170
Leu-Val-Arg-Gln-Ile-Asn-Arg-Lys-Thr-Pro- 171                 175                      180
Val-Glu-Lys-Lys-Lys-Pro-Lys-Lys-Lys-Ser- 181       184
Cys-Leu-Leu-Leu
```

Fig. 3

```
CCACATCATGCGTGAGTACAAGCTAGTGGTCCTTGGTTCAGGAGGCGTGGGGAAGTCTGC
TCTGACAGTTCAGTTGTTCAGGGAATTTTTGTTGAAAAATATGACCCAACGATAGAAGA
TTCCTACAGAAAGCAAGTTGAAGTAGACTGCCAACAGTGTATGCTCGAAATCCTGGACAC
AGCGGGAACAGAGCAATTTACAGCAATGAGGGATTTGTATATGAAGAATGGCCAAGGGTT
TGCACTAGTATATTCTATTACCGCTCAGTCCACATTTAATGACTTACAAGACCTGAGGGA
ACAGATTTTACGAGTTAAGGACACAGAAGATGTTCCAATGATTTTGGTTGGCAATAAGTG
TGACCTGGAAGACGAGCGAGTAGTTGGCAAAGAACAGGGTCAGAATTTAGCAAGACAGTG
GTGTAACTGTGCCTTTTTAGAATCTTCTGCAAAGTCAAAGATCAACGTTAATGAGATATT
TTATGACCTGGTCAGACAGATAAATAGAAAAACACCAGTGGAAAGAAGAAGCCTAAAAA
GAAATCGTGTCTGCTCTTTAGCCCACAGTAAGCAGCAGCTCTGAGCCAGATTACAGGA
ATGAAGAACTGTTGCCTAATTGGAAAGTGCCAGCATTCCATACTTCAAAATAAATCTGA
AGAGGCTTCTCCTGTTTTATATATTATGTGAAGAATTTAGATCTTATATTGGTTTGCACA
AGTTCCCTGGAGAAAAGAATTGCTCTGTGTATATCTCTTGGAAAATAAGACAATAGTATT
TCTCCTTTGCAATAGCAGTTATAA
```

MUTANT SMG P21 PROTEIN WITH GTP BINDING ACTIVITY

This is a divisional of copending application Ser. No. 07/814,205 filed on Dec. 20, 1991, which is a continuation of 07/358,835, filed May 30, 1989, now abandoned.

BACKGROUND OF THE INVENTION

1. Field of the Invention

The present invention concerns a novel GTP binding protein (Smg p21) which gives an inhibitory effect on ras oncogene products, and a method for producing said protein by utilizing recombinant DNA technology.

2. The Prior Art

Each of cells constituting an individual mammal play its own role in such a fashion that the cell always receives extracellular information or stimulation, and responses thereto.

An information conversion unit on a cell membrane for receiving information given to each of cells by so-called primary information-transmitting substance consists of three kinds of proteins, i.e., a receptor, a transducer and an effector. GTP (guanosine-5-triphosphate) binding protein (hereinafter referred to as "G protein") functions as the transducer among them. That is, when the receptor receives primary information from outside of a cell, it acts on an inactive GDP-G protein, by which the GDP bonded to G protein is converted into GTP to form an active GTP-G protein. Then, the active GTP-G protein gives an effect on the effector and information (secondary information) is transmitted from the effector to the inside of the cell.

For the G protein, there have been known, for example, functions of high molecular weight G protein (molecular weight of about 40,000) consisting of various proteins (subunits). Recently, the presence of low molecular weight G protein has been revealed.

There are present at least 15 kinds of the low molecular weight G proteins, i.e., G proteins with molecular weight of from 20,000 to 25,000. The present inventors have previously succeeded in purifying G protein with molecular weight of 24,000 (Smg p25A) and G protein with molecular weight of 22,000 (Smg p21:22K dalton) as single protein in SDS-PAGE and reported details for the G protein of Smg p25A (refer to Experimental Medicine, vol. 6, No. 5, p 34–42, 1988: Journal of the Biological Chemistry, 263, p 2897–2904, 1988).

However, the structure and function of such G proteins have not yet been revealed in detail.

Furthermore, Smg p21 can be purified only by an amount of about several tens of micrograms by using a conventional methodology in protein chemistry. Accordingly, it has been difficult to use them in a great amount for the pharmaceutical test such as of anti-cancer agents. Further, it has still been considered impossible to introduce artificial mutation, thereby preparing Smg p21 variant protein with a high anti-ras activity.

SUMMARY OF THE INVENTION

In order to determine or clarify the entire structure and the function of the G protein with molecular weight of 22,000, the present inventors have succeeded for the first time in obtaining the G protein with molecular weight of 22,000 in a great amount as a single molecule species by purifying said G protein, determining its partial amino acid sequence to prepare a probe, cloning cDNA of said G protein from a cDNA library of G proteins, determining the base sequence thereof and constructing an expression vector containing said cDNA.

That is, an object of the present invention lies in providing a GTP binding protein containing the following amino acid sequence, with a molecular weight of about 22K dalton and having GTP binding activity and GTP hydrolyzing activity in which the GTP binding activity is inhibited by N-ethylmaleimide:

Thr-Ile-Glu-Asp-Ser-Tyr, especially, a GTP binding protein represented by the amino acid sequence shown in FIG. 1.

A further object of the present invention is to provide a method for the production of Smg p21, which comprises introducing a DNA fragment containing DNA that encodes the GTP binding protein into a cloning site present at the downstream to a promoter of an expression vector, then introducing the expression vector thus constructed into a host, culturing the host, thereby expressing and accumulating the GTP binding protein and then collecting thereof.

The present invention is to be described more specifically.

DETAILED DESCRIPTION OF THE INVENTION

The G protein in accordance with the present invention is present in cytoplasmic membranes of mammalian cells.

For instance, G protein with molecular weight of about 22K dalton can be purified by pulverizing bovine brain to obtain a fraction of cell membrane, extracting a crude membrane fraction with sodium cholate, and then succesively subjecting it to Ultrogel AcA-44 (manufactured by LKB Co.) column chromatography, phenyl-Sepharose CL-4B (manufactured by Pharmacia LKB Co.) column chromatography, hydroxyapatite (manufactured by Seikagaku Kogyo Co.) column chromatography, Mono Q HR 5/5 (manufactured by Pharmacia LKB Co.) column chromatography, Mono S HR 5/5 (manufactured by Pharmacia LKB Co.) column chromatography and then again to Mono Q HR 5/5 column chromatography, as shown in EXAMPLE to be described later.

The G protein thus purified has GTP binding activity and GTP hydrolyzing activity. Although the GTP binding activity may be inhibited by N-ethylmaleimide, the presence of dithiothreitol would block such inhibition.

Further, the G protein of the present invention shows no cross reaction with an anti-ARF (ADP-ribosylation Factor) polyclonal antibody and an anti-ras p21 monoclonal antibody.

According to the present invention, the partial amino acid sequence of said purified G protein is determined to prepare a probe and cDNA of said G protein is cloned from the cDNA library prepared from the entire poly A RNA by a conventional method.

From the cloned cDNA, a DNA fragment that encodes the G protein with molecular weight of about 22K dalton is obtained to determine its base sequence (FIG. 3).

It has been found from the base sequence that the G protein according to the present invention is a protein comprising 184 amino acid residues. Further, the G protein according to the present invention has about 77% homology with ras protein for 44 amino acid residues at N-terminals and about 53% homology for the entire portion. And it has been found that they share a region of the same sequence at 35-40 (Thr-Ile-Glu-Asp-Ser-Tyr) in which region ras protein is assumed to act with the effector.

The method for the production of the G protein according to the present invention is to be explained.

The DNA fragment which may be used in the present invention includes, in addition to DNA represented in FIG. 3, many derivatives in which a portion of its base sequence may be replaced or deleted or other base may be added in the base sequence, so long as the substance encoded by DNA contained in the DNA fragment has the same physiological activity as Smg p21. For instance, there may be mentioned the DNA that encodes the amino acid sequence shown in FIG. 1 in which the 12th Gly is substituted with Val, the 38th Asp is substituted with Ala and the 40th Tyr is substituted with Lys.

In addition, various amino acid replacements may be included in the amino acid sequence of the G protein according to the present invention, which are summarized in TABLE 1 below.

TABLE

| Original Residue | Representative Substituent Residue |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

The above DNAs which encode the modified G protein according to the present invention may be prepared by a known method such as site-specific mutation using a synthetic oligonucleotide or by a conventional method of ligating a restriction fragment and synthetic one.

The expression vector in the present invention contains a promoter at a suitable position so that it may regulate transcription of the DNA that encodes Smg p21 obtained as described above.

Any promoter may be used so long as it can express Smg p21 in a host, a controllable promoter being further preferred.

For instance, when using as the host microorganisms such as *Escherichia coli* and *Bacillus subtilis*, the expression vector preferably comprises promoter, ribosome binding sequence, Smg p21 gene, transcription termination factor and a gene for controlling the promoter.

As the promoter, there can be mentioned those derived from *Escherichia coli*, phage, etc., for example, triptophan synthetase operon (trp), lactose operon (lac), lipoprotein (lpp), rec A, lambda phage, $P_L$, $P_R$ and T5 early gene $P_{25}$, $P_{26}$ promoters. They may be chemically synthesized. Further, hybrid promoters such as of tac (trp:lac), trc (trp:lac) pac (phage:*Escherichia coli*), may also be used.

As the ribosome binding sequence, those derived from *Escherichia coli* and phage may be used, but those having consensus sequence synthetically prepared, for example, those having a sequence such as

|AGGA|GGTTTAA

SD sequence are preferred.

Although the Smg p21 gene may be used as it is, those lacking an unnecessary DNA sequence (non-coding region) by site-specific mutation (Bio Technology, July, p 636–639 (1984)) and the like are preferred.

Although the transcription termination factor is not always necessary, it is preferred for the expression vector to have ρ-independent one, for example, lpp terminator, trp operon terminator, terminator of ribosome RNA gene.

Further, usual plasmids may be used for the expression vector of the present invention. Plasmids which may provide a multiple copy in *Escherichia coli* or *Bacillus subtilis*, for example, those derived from pBR 322 or pUB 110 plasmid may preferably be used.

Further, for the sequence order on the expression plasmid, of these factors necessary for the expression, it is desired that they are arranged in the order of promoter, SD sequence, Smg p21 gene, structural gene and transcription termination factor from the upstream at 5' end. There is no particular restriction for the order of the repressor gene required for the control of transcription, marker gene drug resistance gene, etc.), initiation site of the plasmid replication and the like. Further, the transcription efficiency can be increased by arranging in tandem and ligating a connected sequence of SD and Smg p21 gene to the downstream of the promoter. As a result, improvement in the yield and quality of the produced protein can be expected.

For transformation of the host, usual methods may be used, for example, a method as described in Molecular Cloning, p 250-253, (1982) for *Escherichia coli* and methods as described in Molecular General Genetics, 168, p 105–115 (1979) and in Proceeding National Academy of Science, U.S.A., 44, p 1072–1078 (1958) for *Bacillus subtilis*.

For a method of culturing a transformant, those culture media capable of conducting usual culture both for *Escherichia coli* and *Bacillus subtilis* (Molecular Cloning, p 68–73 (1972)) may be used. The culture may be conducted at a temperature from 15° to 42° C. and, preferably, within a range causing no induction of the expression of heat shock protein and the like (15°–25° C.).

In eucaryotic cells such as, for example, animal cells, the following conditions are preferred.

Preferred promoters include SV40 early promotor, SV40 late promoter, promoter of apolipoprotein E gene, promoter of apolipoprotein A-I gene, promoter of heat shock gene (Proceeding National Academy of Science, U.S.A.) 78, p 7038–7042 (1981)), promoter of metallothionein gene (Proceeding National Academy Science, U.S.A., 77, p 6511–6515, (1980)), HSVTK promoter, promoter of adenovirus (Ad 2 major late promoter (Ad 2MLP promoter)), LTR (long Terminal Repeat) of retrovirus, etc., the SV40 promoter and the metallothionein gene promoter being particularly preferred.

The expression vector may contain a splice sequence DNA consisting of 5' splice site (5' splice junction doner site), intron and 3' splice site (3' splice junction acceptor site), and intron, in which a common base sequence has been found at exon-intron junction site and the periphery of such junction site, that is, a so-called GT/AG rule has been established that the intron region always begins with 2 base (at donor site) of GT and ends with 2 base (at acceptor site) of AG.

One or more of such splice sequence DNA may be present in the expression vector and they may be located either to the upstream or downstream of Smg p21 gene.

As specific examples of the splice sequence DNA, there can be mentioned those splice sequence DNA present in exson 2 and exson 3 of rabbit β-globin gene (Science, 26, p 339 (1979)) and promoter, exson 1, 2 and 3 of metallothionein gene and mouse metallothionein-I gene containing introns A and B (Proceeding, National Academy of Science, U.S.A., 77, 6513, (1980)). Further, 5' and 3' splice sites are not necessarily derived from an identical gene, but a sequence in which 5' splice site contained in adenovirus DNA and 3' splice site derived from Ig variable region gene are ligated together may be alternatively used for instance.

The expression vector in the present invention may further contain a polyadenylation site. The polyadenylation site is present downstream of Smg p21 gene. As specific examples of the polyadenylation site, those derived from SV40 DNA, β-globin gene or methallothionein gene may be mentioned. Further, the polyadenylation site may be prepared by ligating polyadenylation sites of β-globin gene and SV40 DNA together.

The expression vector in the present invention may have a dominant selective marker allowing the selection of transformant. If there is no selective marker in the expression vector, the transformed animal cells of the present invention can be selected by cotransformation.

As for the selective marker, there can be mentioned DHFR gene giving MTX (methotrexate) resistance, tk gene of herpes simplex virus (HSV) allowing the selection of a transformed tk⁻ strain in HAT medium, aminoglycoside 3'-phosphor transferase gene from transposon Tn5 of *Escherichia coli* providing resistance to 3'-deoxystreptamine antibiotic G418, bovine papilloma virus gene enabling morphological distinction by piled up growth, aprt gene, etc.

For selecting animal cells transformed with the expression vector in the present invention by the cotransformation method, the transformed cells can be selected by transforming animal cells with a plasmid containing the selective marker gene together with the expression vector and selecting the transformed cells based on phenotypes which have appeared by the expression of the selective marker.

It is advantageous if the expression vector contains plasmid fractions having a replication origin derived from cells such as *Escherichia coli*, since it may be cloned in bacteria. pBR 322, pBR 327, pML and the like may be mentioned as examples for such plasmid vector.

As the specific examples of plasmid vectors used for the expression vector in the present invention, there can be mentioned pKCR containing SV40 early promoter, splice sequence DNA derived from rabbit β-globin gene, polyadenylation site from rabbit globin gene, polyadenylation site from SV40 early region and replication origin from pBR 322 and ampicilin resistance gene (Proceeding National Academy of Science, U.S.A., 78, p 1528 (1981)), pKCR H2 in which the pBR322 in pKCR is substituted with pBR327 site and Eco RI site present in exon 3 of rabbit β-globin gene is replaced by HindIII site (Nature, 307, p 605), pBPVMT1 containing BPV gene and metallothionein gene (Proceeding National Academy of Science, U.S.A., 80, p 398 (1983)), etc.

As animal cells to be transformed with the expression vector, there can be mentioned CHO cells, COS cells, mouse L cells, mouse C127 cells, mouse FM3A cells, etc.

The expression vector of the present invention may be introduced into the animal cells, most generally, by way of transfection, micro injection, Ca—PO₄ method (Virology, 52, p 456–467 (1973)).

Culture of the transformed animal cells may be carried out by a conventional method such as in suspension culture medium or fixed culture medium.

As the culture medium, MEM, RPMI 1640 and the like may be generally used.

The protein thus produced can be separated and purified in the same manner as that used with transformed microorganisms.

As has been described above, since the DNA of the present G protein with molecular weight of about 22K dalton has extremely high homology (55%) with an oncogene ras, there is a possibility that they may act the same effector. Accordingly, it is considered that the G protein according to the present invention may control an oncogene product protein RAS directly or indirectly, and may be expected to act as an inhibitor against oncogenic effect of RAS.

DESCRIPTION OF THE DRAWINGS

FIGS. 1(i) and 1(ii) illustrate an example of an amino acid sequence for the G protein (Smg p21) according to the present invention.

FIG. 3 illustrates a base sequence of the cloned cDNA for the G protein in Example 1.

The present invention is to be described more in details referring to Examples but it should be noted that the present invention is not restricted only thereto unless they does not exceed the scope thereof.

EXAMPLE 1

(1) Purification of G Protein with Molecular Weight of 22,000 (Smg p21) (refer to Table 2)

(a) Crude G protein with molecular weight (relative molecular weight: Mr) of 20,000 to 25,000 was obtained in accordance with the method of Kikuchi, et al. (Journal of the Biological Chemistry, 263, p 2897–2904, 1988).

Specifically, a crude membrane fraction was extracted with sodium cholate from bovine brain, and the fraction was fractionated on Ultrogel AcA-33 column chromatography to separate and obtain a fraction at the second peak among two peaks showing GTP binding activity. The fraction thus obtained was purified on phenyl Sepharose CL-4B column chromatography and then further fractionated on hydroxyapatite column chromatography to separate and obtain a fraction at the first peak. Then, the first peak fraction was fractionated on Mono Q HR 5/5 column chromatography and the fraction at the first peak was separated and collected to obtain a crude G protein with Mr of 20,000–25,000.

Figure 2:
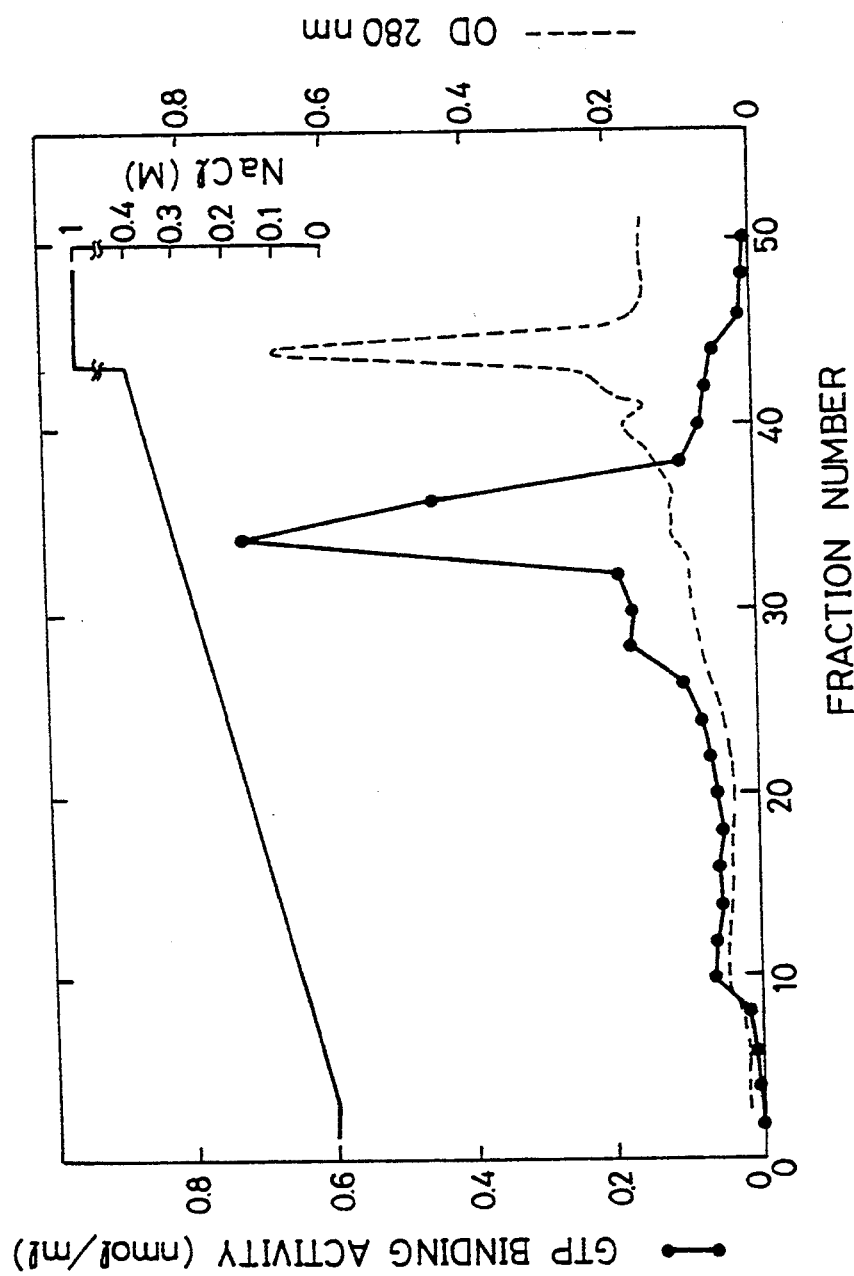
FIG. 2 shows an elution pattern in Mono Q HR 5/5 column chromatography (the second time) in Example 1.

(b) The crude G protein obtained in (a) above was subjected to Mono S HR 5/5 column chromatography equilibrated with a buffer solution of 50 mM sodium acetate (pH, 5.0) containing 1 mM EDTA, 1 mM dithiothreitol, 5 mM magnesium chloride and 0.6% CHAPS (3-[(3-cholamidopropyl) dimethylammonio]-1-propane sulfonate). After washing with 5 ml of the same buffer solution, it was eluted out by the same buffer solution (20 ml) with a concentration gradient of sodium chloride (0–1.0M). Elution was carried out at a flow rate of 0.5 ml/min and eluate was fractionated into 0.5 ml each. When the DTP binding activity was examined for each of the fractions, four peaks were observed. Among them, the fourth peak (50–68 fractions) was collected, diluted ten times with a buffer solution of 20 mM trishydrochloric acid (pH, 9.0) containing 1 mM EDTA, 1 mM dithiothreitol, 5 mM magnesium chloride and 0.5% sodium cholate, and subjected to Mono Q HR 5/5 column chromatography equilibrated with the same buffer solution. After washing with 5 ml of the same buffer solution, it was eluted out by the same buffer solution (20 ml) with a concentration gradient of sodium chloride (0–0.4M). Elution was conducted out at a flow rate of 0.5 ml/min and eluate was fractionated each by 0.5 ml. The elution pattern is shown in FIG. 2. When fractions with fraction numbers of 10–20 were collected and subjected to SDS-polyacrylamide (8–16%) gel electrophoresis, they showed a single band for about 22K dalton of molecular weight. Thus, purified G protein (Smg p21) was obtained. Various properties of the G protein (Smg p21) are as shown in TABLE 3.

TABLE 2

| Purification Step | ml | Total Protein ml | Total GTP Binding Activity nmol | Specific Activity nmol/mg | Yield % |
|---|---|---|---|---|---|
| Sodium Cholate Extraction | 95 | 858 | 484 | 0.56 | 100 |
| Ultrogel AcA-44 (second peak) | 200 | 90 | 223 | 2.5 | 46 |
| Phenyl Sepharose CL-4B | 120 | 32 | 142 | 4.4 | 29 |
| Hydroxyapatite (first peak) | 240 | 6.8 | 51 | 7.5 | 11 |
| Mono Q HR 5/5 (first peak) | 8 | 0.95 | 10 | 11 | 21 |
| Mono S HR 5/5 (fourth peak) | 9.5 | 0.23 | 4.6 | 20 | 0.95 |
| Mono Q HR 5/5 (second time) (first peak) | 5.5 | 0.011 | 0.36 | 33 | 0.074 |

TABLE 3

|  | G Protein |
|---|---|
| Mr | 22,000 |
| Kd of GTP Binding Activity (nM) | 30 ± 6 |
| GTP Hydrolyzing Activity (number of turnovers, mm$^{-1}$) | 0.005 + 0.002 |
| Effect of N-ethylmaleimide on GTP Binding Activity | inhibited |
| Cross Reaction with Anti-ARF Polyclonal Antibody | none |
| Cross Reation with Anti-RAS P21 Monoclonal Antibody | none |

(2) Determination of the Amino Acid Sequence of G Protein (Smg p21)

(a) Preparation of Probe

After desalting 25 μg of the purified G protein (Smg p21) obtained in (1) above on Sephadex G-25 chromatography, it was subjected to YMC pack AP-802 C4 column chromatography equilibrated with 0.1% trifluoroacetic acid. Then, it was eluted out with 40 ml of 0.1% trifluoroacetic acid having a concentration gradient of acetonitrile/2-propanol (3/7) of from 0 to 100%, at a flow rate of 1 ml/2 min. The G protein in the resultant fractions was digested with Achromobacter lyticus protease I, which was fractionated on Bakerbond WP Oc-'tyl column chromatography. The determination of the amino acid sequence for one of said fractions by a gas phase sequencer (Model 470A, manufactured by Applied Biosystems Co.) has revealed that a peptide contained therein has 18 amino acids as shown below.

Asn-Gly-Gln-Gly-Phe-Ala-Leu-Val-Tyr- Ser-Ile-Thr-Ala-Gln-Ser-Thr-Phe-Asn

Subsequently, an oligonucleotide mixture of the following base sequences was chemically synthesized as a probe based on the sequence: Asn-Gly-Gln-Gly-Phe-Ala (Model 380A, manufactured by Applied Biosystems Co.).

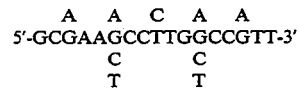

Then, the 5' terminal of the resulting probe was labelled with $^{32}$P by using T4 polynucleotidekinase (manufactured by TOYOBO CO., LTD.) and γ-$^{32}$P-ATP.

(b) Preparation of G Protein (Smg p21) cDNA

RNAs having poly(A) were prepared as described below from bovine cerebrum by guanizine thiocyanate-lithium chloride method (Cathala, et al. DNA, 2, p 329, 1983).

Specifically, 5 g of bovine cerebrum was directly frozen in liquid nitrogen, which was then charged together with liquid nitrogen into a whirling blender and pulverized for 2 min at 3,000 rpm. The resulting powder was further pulverized and solubilized in 100 ml of a solution comprising 5M guanizine thiocyanate, 10 mM EDTA, 50 mM tris-hydrochloric acid (pH 7) and 8% (V/V) β-mercaptoethanol, using a teflon homogenizer (5 rpm). 20 ml of the solubilized material was quietly placed on 10 ml of a 57M cesium chloride solution in a centrifugal tube, centrifuged at 27,000 rpm for 20 hours by Hitachi RPS28-2 rotor and then RNAs were recovered as precipitates. The RNA precipitates were dissolved in 10 ml of a solution comprising 0.1% sodium lauryl sulfate, 1 mM EDTA and 10 mM tris-hydrochloric acid (pH 7.5), extracted with phenol-chloroform and then recovered by ethanol precipitation. About 3.95 mg of the resultant RNA was dissolved in 1 ml of a solution comprising 10 mM of tris-hydrochloric acid (pH 8.0) and 1 mM EDTA, incubated at 65° C. for 5 min and mixed with 0.1 ml of 5M sodium chloride. The mixture was subjected to oligo (dT) cellulose-column chromatography (column volume of 0.5 ml) (manufactured by P-L Biochemical Co.).

mRNA having an adsorbed poly (A) was eluted out with a solution comprising 10 mM tris-hydrochloric acid (pH, 7.5) and 1 mM EDTA to obtain about 100 μg of mRNA having poly (A).

By using about 5 μg of the poly(A) mRNA thus obtained, a library of bovine brain cDNA (λgt 10 vector) was prepared in accordance with the method as described in a manual of Amersham Co. "cDNA Synthesis System", p 13–21 and "cDNA Cloning System λgt 10", p 11–28. From the resulting cDNA library, a plaque hybridized with the labelled probe obtained in (a) above on a nitrocellulose filter (manufactured by S & S Co.) was detected by the method of D Hanahan, et al (Methods in Enzymology, 100, p333–342, 1983) to obtain 1 clone of λgt 10 hage integrated with the cDNA coding for the G protein (Smg p21).

The resulting phage DNA was digested with Eco RI to obtain about 2 Kb of Eco RI fragment, which was inserted into an Eco RI site of plasmid pUC 19 (Gene, 33, p 103–119, 1985) to clone DNA that encodes the G protein (Smg p21). The resultant plasmid was defined as pSmg 21. The base sequence of the thus obtained DNA was determined by the dideoxy method of Sanger, et al (Proceeding of the National Academy of Science, U.S.A., 74, p 5463–5467, 1977). The results are shown in FIG. 3.

From the base sequence described above, it was found that the G protein (Smg p21) the entire amino acid sequence as shown in FIG. 1.

EXAMPLE 2

A: Preparation of Expression Vector and Transformant

1) Mutation at N terminal
   (1) pSmg 21 was treated by the method as described in the catalogue of Takara Shuzo Co. in 1988 (p 82 and 83) to obtain 10 μg of a single strand DNA.
   (2) A primer of the following portion to be used for mutation was synthesized in a DNA synthesizer (Applied Biosystem Model 380A, manufactured by Nikkaki Co.). The synthesized DNA was reacted with a concentrated aqueous ammonia at 55° C. over one night to remove a protective group and purified by a reverse-phase HPLC.

Primer:

5'-CGGCCAGTGAATTCC

AAGCTTATGAGAGAATATAAACTAGT

GGTCCTTGG-3'

150 pmol of the primer was phosphorylated at 5' end with 20 units of T4 polynucleotide kinase in a system comprising 10 μl of a kinase buffer solution (50 mM of tris-HCl (pH, 8.0), 10 mM magnesium chloride and 5 mM dithiothreitol).
   (3) Then, a mutant having a double strand DNA was prepared from 8 pmol of the 5'-phosphorylated primer in (2) and 10 μg of the single strand DNA obtained in (1) above in a system for preparing a mutant with site-specific mutation in vitro using oligonucleotide of Amersham Co., in accordance with an manual of Amersham Co. (p 25–32, 1988).

By using 2 μl of an aqueous solution containing the resulting circular DNA, *Escherichia coli* HB 101 strain was transformed in accordance with a customary method to obtain a transformant. The plasmid was separated and purified from the transformant by a customary method, which was then cleaved by a restriction enzyme HindIII to obtain two fragments as a mutant plasmid by means of 5% acrylamide gel electrophoresis. In this way, plasmid pSmg 21-1 was obtained.

Figure 4:
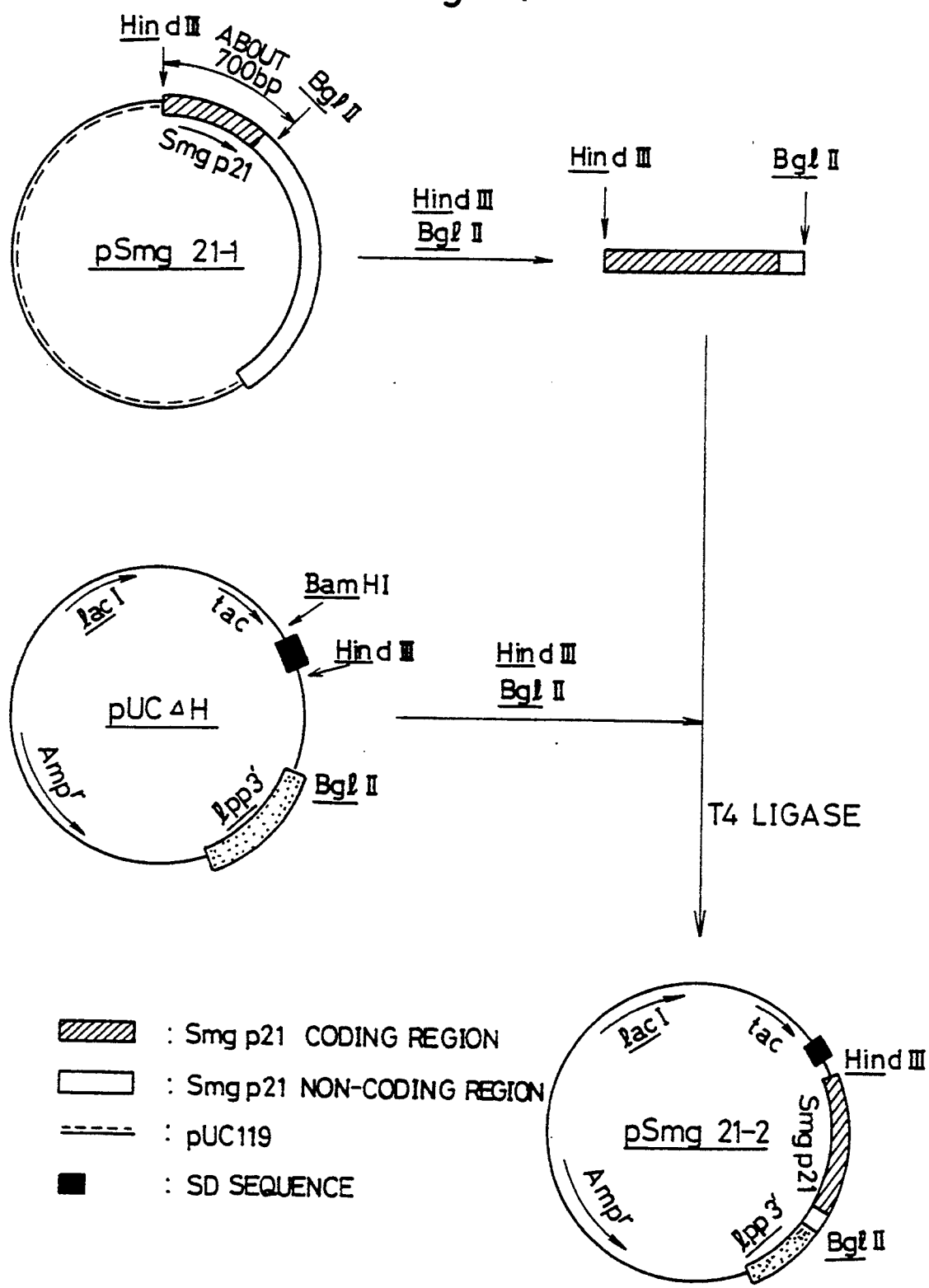
FIG. 4 represents a schema showing the preparation steps of plasmid pSmg 21-1 and pSmg 21-2 in Example 2.

2) Introduction of Smg p21 cDNA into Expression Vector
   (1) 10 μg (~3 pmol) of pSmg 21-1 was cleaved by using 20 units of HindIII and 20 units of Bgl II at 37° C. for 2 hours in 100 μl of a buffer solution H (10 mM trishydrochloric acid (pH, 7.5), 100 mM sodium chloride and 6 mM magnesium chloride). The cleaved plasmid was subjected to 5% acrylamide gel electrophoresis to separate and purify an about 700 bp DNA fragment that encodes Smg p21. - - - Fragment N.
   (2) 2 μg of pUS ΔH (~1 pmol) as an expression vector was cleaved using 2 units of HindIII and 2 units of Bgl II in a 20 μl of the buffer solution H at 37° C. for 2 hrs. The reaction product was extracted and deproteined with water-saturated phenol of an equivolume. After extracting phenol with ether, the extracted product was dialyzed against, to water, desalted and then concentrated by a vacuum pump to obtain 10 μl of an aqueous solution containing an expression vector fragment HB.
   (3) 0.5 pmol of Fragment N and 0.1 pmol of the expression vector fragment HB were mixed and treated with 1 unit of T4 DNA ligase at 4° C. in 10 μl of a buffer solution comprising 10 mM of trishydrochloric acid (pH, 7.5), 1 mM dithiothreitol, 6 mM magnesium chloride and 1 mM ATP. 3 μl of the resulting vector was used for transforming commercially available *Escherichia coli* JM 109 competent cells by a conventional method. The transformant was selected in L-culture medium containing 20 μg/ml of ampiciline (10 g/l of bactopeptone, 5 g/l of yeast extract, 10 g/l of sodium chloride and 15 g/l of agar) to obtain the expression vector pSmg 21-1 in which a gene encoding a specific antigen had been inserted (FIG. 4).

B: Expression of Smg R21

*Escherichia coli* YA21 strain carrying pSmg 21-2 was cultured in L-broth at 30° C. over one night. Then, it was inoculated to M9 culture medium (adjusted to pH 7.4 with 6 g/l of disodium hydrogenphosphate, 3 g/l of sodium dihydrogenphosphate, 0.5 g/l of sodium chloride and 1 g/l of ammonium chloride and then supplemented with 2 ml of 1M magnesium sulfate, 10 ml of 20% glycerol and 0.1 ml of 1M calcium chloride) so as to be diluted 50 times and cultured under shaking at 30° C. for 2 hours. Then, IPTG (isopropyl-β-D-galactopyranoside) was added to the culture medium to a final concentration of 2 mM. After incubated under shaking at 30° C. for 16 hours, bacteria were collected by centrifugation at 6,500 rpm for 10 min. They were suspended and maintained in a buffer solution comprising 0.9% sodium chloride and 10 mM tris-hydrochloric acid (pH, 7.5).

C: Confirmation of the Expression of Smg p21

After subjecting 0.3 ml of the cultured cell bodies obtained in (B) above to 10% SDS polyacrylamide gel electrophoresis (in a buffer solution comprising 3 g/l of tris, 14.4 g/l of glycine and 0.1% of SDS, at 120 V for one hour), the gel was taken out and dyed with Coomassie Brilliant Blue (Sigma Co.) by an usual method. As a result, a new band which was not found for cell bodies cultured without induction of IPTG was detected at the region for a molecular weight of about 22,000, which was expected to be Smg p21. Then, the gel corresponding to the new band was cut-out and again subjected to electrophoresis in the same buffer solution to elute out a protein into the buffer solution. When an amino acid sequence for the eluted protein was determined from the N-terminal by an amino acid sequencer (manufactured by Applied Bio-Systems Co.), it was revealed that the protein was identical to Smg p21 as far as N-terminal 20 amino-acid sequence.

Further, when the resultant protein was reacted with an anti-Smg p21 mouse monoclonal antibody on a nitrocellulose filter, washed, labelled with iodo-labelled protein A, it was found that the protein may react with the anti-Smg p21 mouse monoclonal antibody.

From the above results, it was confirmed that the resultant protein was Smg p21.

EXAMPLE 3

10 μg of the plasmid pSmg 21-2 obtained in Example 2 was cleaved with each 10 units of Bam HI and Bgl, while being kept together at a temperature of 37° C. for 2 hours.

Figure 5:
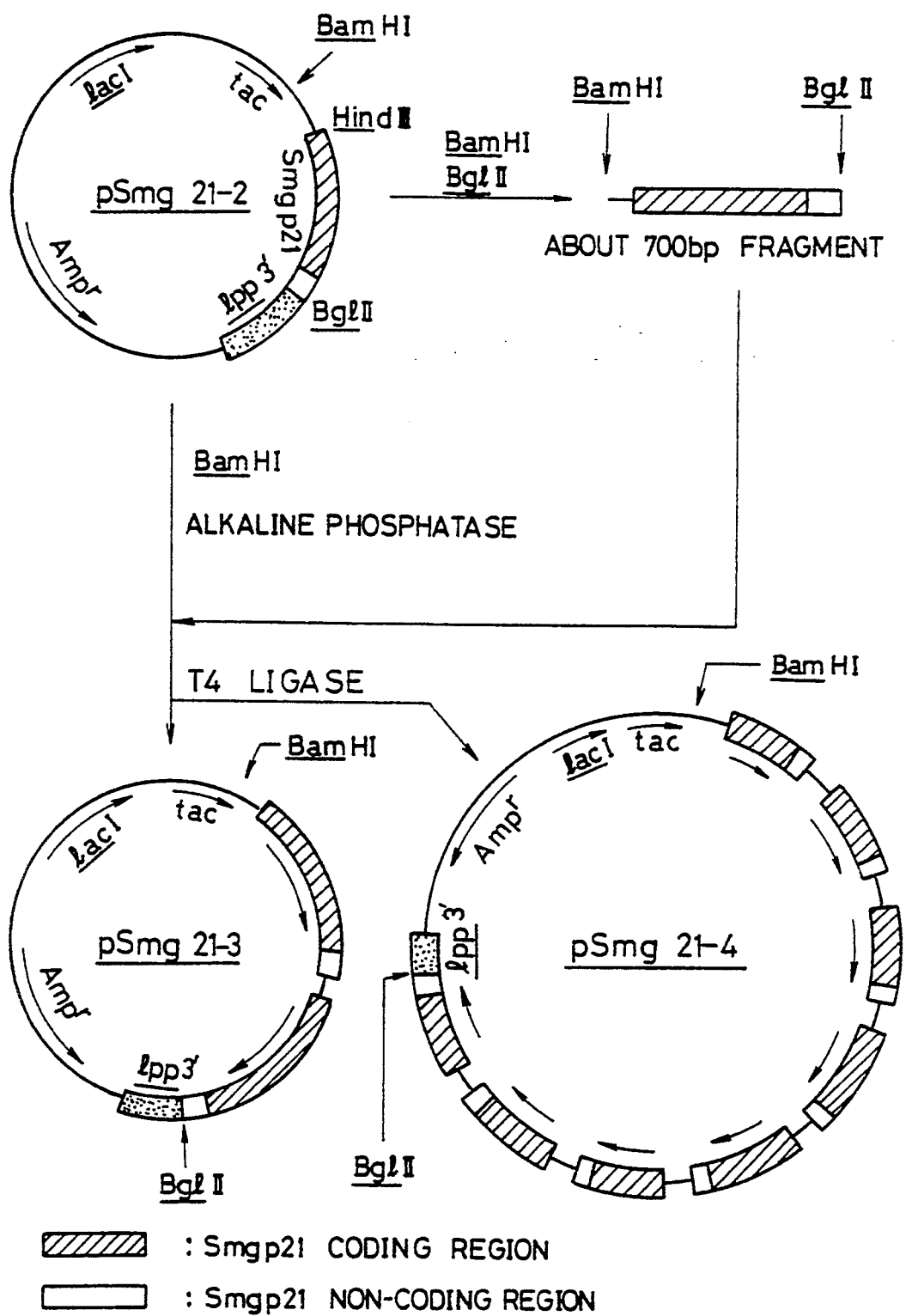
FIG. 5 represents a schema showing the preparation steps of plasmid pSmg 21-3 and pSmg 21-4 in Example 3.

The reaction product was subjected to 4% polyacrylamide gel electrophoresis and a Bam HI and Bgl II fragment of about 700 bp was cut-out from the gel and purified. Separately, 10 μg of plasmid pSmg 21-2 was cleaved with 10 units of Bam HI while being kept at a temperature of 37° C. for 2 hours and, thereafter, maintained at 65° C. for one hour together with 2 units of alkaline phosphatase to remove a terminal phosphoric group. Then, phenol extraction and ethanol precipitation were conducted for purification. 0.1 μg of the plasmid thus purified was ligated with the above Bam HI and Bgl II fragment by using T4 ligase. Among the various resultant plasmids, plasmids pSmg 21-3 and 21-4 having two Smg p21 genes or more were obtained (FIG. 5).

*Escherichia coli* YA 21 strain was transformed with pSmg 21-3 and pSmg 21-4 respectively to obtain transformed *Escherichia coli* strains producing Smg p21.

After culturing these *Escherichia coli* strains at 30° C. for one day in 10 ml of LB broth (10 g/l of bactotryptone, 5 g/l of bactoyeast extract and 10 g/l of sodium chloride: pH, 7.5), they were inoculated to 1 liter of M9 culture medium and cultured under shaking at 19° C. for 2 hours. Then, IPTG was added to a final concentration of 2 mM and further cultured under shaking at 19° C. over one day and night, by which Smg p21 recovered in soluble fractions could be produced. The soluble fraction means herein a fraction prepared by collecting bacteria after culture, and subjecting them serially lysozyme treatment at a lysozyme concentration of 10 mg/l, supersonic pulverization for 2 min using a Sonicator (manufactured by Bulanson Co.) and then centrifugation to the thus obtained cell bodies in a solution at a final concentration of 0.1% triton×100 and 1.5M of sodium chloride at 15,000 rpm for 10 min and then recovering a resulting supernatant. When the activity of the soluble fraction with the anti-Smg p21 mouse monoclonal antibody was examined in the same manner as in Example 1, it was found that the fraction contained protein capable of binding with said antibody.

EXAMPLE 4

A: Preparation of Expression Vector

After digesting 10 μg of pSmg 21 with 10 units of Eco RI, it was separated by 0.7% agarose gel electrophoresis and agarose gel portion containing an about 2.5 Kbp DNA fragment was cut out and DNA was extracted from the gel by a freeze-thawing method.

The extracted DNA was purified by repeating phenol extraction and ethanol precipitation.

Figure 6:
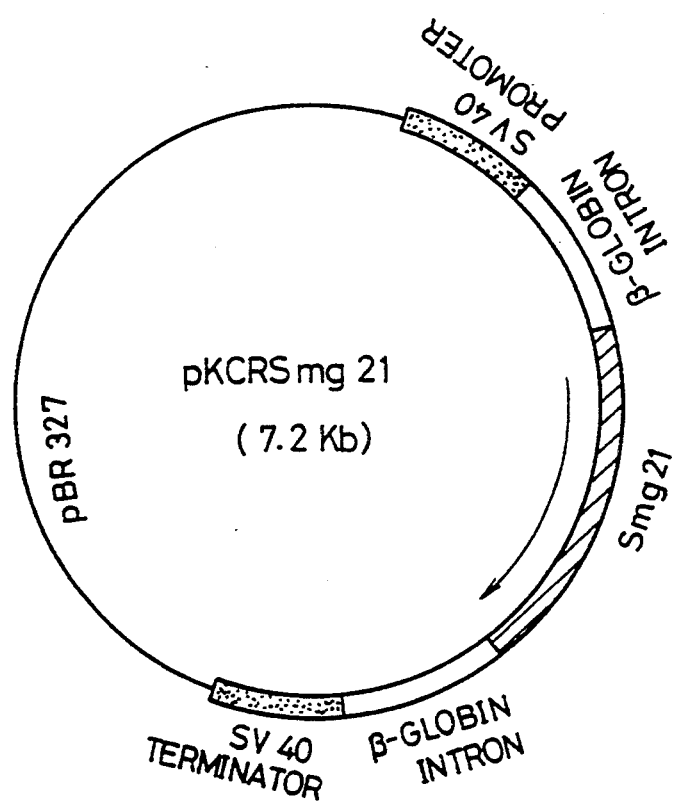
FIG. 6 represents an outline for the structure of the expression vector pKCR Smg 21 prepared in Example 4.

0.5 μg of the DNA was reacted with 0.1 μg of a pKCR vector previously digested with Eco RI and treated with alkaline phosphatase treatment (Japanese Patent Application Laid-Open (KOKAI) No. 285990/86) in the presence of 5 units of T4 DNA ligase at 16° C. over one day and night to obtain an expression vector pKCR Smg 21, which is shown in FIG. 6.

B: Expression of Smg p21 in COS Cells

20 μg of pCKR Smg 21 obtained in (A) above was added to a dish (6 cm in diameter) containing COS cells (about 1×10⁶ cells) cultured in a semi-confluent state and introduced into the COS cells by a calcium phosphate method in accordance with the method of Okayama, et al. ("Molecular and Cellular Biology", 17, p 2745–2752, 1987). After introduction, they were cultured in $CO_2$ atmosphere at 37° C. over three days and nights to obtain about 2×10⁷ cells.

From the cultured cells thus obtained, total RNA (about 100 μg) was obtained by a GTC-lithium chloride method ("Molecular cloning, first addition", p 188–196, 1982, published from Cold Spring Harbor Laboratory).

Using 20 μg of the RNA, Nothern blotting was applied in accordance with the method of Tomas, et al ("Methods in Enzymology", 100, p 255–266, 1983, published from Academic Press). In this case, an about 660 bp DNA fragment obtained by digesting 1 μg of pSmg 21 with one unit of Eco RI and one unit of Bgl II (Smg p21 coding probe, having all of the Smg p21 coding region therein and labelled with $^{32}P$ by nick translation was used as a probe.

For comparison, COS cells not introduced with pKCR Smg 21 were cultured in the same way and the Nothern blotting was applied by using the total RNA prepared in the same manner as above from the cultured cells thus obtained.

As a result, in the RNA obtained from the COS cells bearing pKCR Smg 21, there was detected RNA to be hybridized with the Smg p21 coding probe in the extra region longer than about 2 Kpb, which was not detected for the RNA obtained from COS cells not transformed with the vector.

Accordingly, it was confirmed that the Smg p21 gene was expressed from pKCR Smg 21.

EXAMPLE 5

A mutant DNA of Smg p21 gene, in which a base sequence coding for Gly (12) is replaced with that coding for Val(12), was prepared and expressed in host cells.

(1) A DNA fragment having the following base sequence:

5'-CTAGTGGTCCTTGGATCC-GTAGGCGTGGGGAAG-3' was prepared by using a DNA synthesizer (manufactured by Applied Bio-Systems Co.). The resulting oligomer (50 pmol) was dissolved in 50 μl of a solution containing 100 mM tris-hydrochloric acid (pH, 8.0), 10 mM magnesium chloride, 7 mM dithiothreitol and 1 mM ATP, treated with 2 units of T4 polynucleotide kinase at 37° C. for 15 min and then incubated at 70° C. for 10 min for inactivation of the enzyme.

(2) *Escherichia coli* JM 109 strains transformed with pSmg 21 were cultured at 37° C. under shaking in 20 ml of YT culture medium (x2) (16 g/l of bactotryptone, 10 g/l of bactoyeast extract, 5 g/l of sodium chloride) containing 100 mg/l of ampicillin and 0.01% of thiamine. When $OD_{600}$ of the culture medium has reached the value of 0.3, the cultured cells were infected by a helper phage M13 K07 with multiplicity of infection (m.o.i.) of 2 to 10. After incubating for 30 min, kanamycin was added to the culture to a final concentration of 70 μg/ml and the incubation was further continued at 37° C. for 10 to 16 hours.

On completion of the culture, cell bodies were precipitated by centrifugation at 2,000 rpm for 10 min to give a supernatant. The resulting supernatant was mixed with 4 ml of 20% polyethyleneglycol and 2.5M sodium chloride, allowed to stand at 4° C. for one hour and centrifuged at 3,000 rpm for 30 min to obtain a precipitate. The resulting precipitate was dissolved in 500 μl of water and centrifuged at 15,0000 rpm for 5 min so as to separate a supernatant. The resulting supernatant was mixed with 200 μl of phenol, shaked and centrifuged at 15,000 rpm for 10 min to obtain a supernatant, to which 50 μl of 3M sodium acetate and 1250 μl of ethanol were added and centrifuged at 15,000 rpm for 10 min to recover a precipitate. The resulting precipitate was dried out and dissolved again in 50 μl of water to give a solution containing pSmg 21 single strand DNA.

(3) An Smg p21 mutant gene in which Val was encoded at 12 instead of Gly was prepared from the phosphorylated oligo-DNA obtained in (1) above and the pSmg 21 single strand DNA obtained in (2) above, based on Oligonucleotide-directed in vitro mutagenesis system according to a manual of Amersham Co., p28–30.

By using a plasmid comprising the above mutant gene (pSmg 21 Val12) in the same manner as for pSmg 21 in Example 2, mutant Smg p21 was expressed in host cells such as *Escherichia coli* and animal cells.

What is claimed is:

1. A purified mutant Smg p21 protein wherein the Gly residue at position 12 of Smg p21 having the formula:

Met-Arg-Glu-Try-Lys-Leu-Val-Val-Leu-Gly- Ser—Gly-Gly-Val-Gly-Lys-Ser-Ala-Leu-Thr- Val-Gln—Phe-Val-Gln-Gly-Ile-Phe-Val-Glu-Lys- Tyr-AsP—Pro-Thr-Ile-Glu-Asp-Ser-Tyr-Arg- Lys-Gln-Val- Glu-Val-Asp-Cys-Gln-Gln-Cys- Met-Leu-Glu-Ile- Leu-Asp-Thr-Ala-Gly-Thr-Glu- Gln-Phe-Thr-Ala- Met-Arg-Asp-Leu-Tyr-Met- Lys-Asn-Gly-Gln-Gly- Phe-Ala-Leu-Val-Tyr-Ser- Ile-Thr-Ala-Gln-Ser- Thr-phe-Asn-Asp-Leu-Gln- Asp-Leu-Arg-Glu-Gln- Ile-Leu-Arg-Val-Lys- Asp-Thr-Glu-Asp-Val-Pro- Met-Ile-Leu-Val-Gly- Asn-Lys-Cys-Asp-Leu-Glu- Asp-Glu-Arg-Val- Val-Gly-Lys-Glu-Gln-Gly-Gln- Asn-Leu-Ala- Arg-Gln-Trp-Cys-Asn-Cys-Ala-Phe- Leu-Glu- Ser-Ser-Ala-Lys-Ser-Lys-Ile-Asn-Val- Asn-Glu- Ile-Phe-Tyr-Asp-Leu-Val-Arg-Gln-Ile- Asn-Arg- Lys-Thr-Pro-Val-Glu-Lys-Lys-Lys-Pro- Lys-Lys- Lys-Ser-Cys-Leu-Leu-Leu is replaced by Val, wherein the mutant has GTP binding activity and GTP hydrolyzing activity and a molecular weight of about 22K dalton.

* * * * *